US00PP26295P3

(12) United States Plant Patent
Korlipara

(10) Patent No.: US PP26,295 P3
(45) Date of Patent: Jan. 5, 2016

(54) ***COREOPSIS* PLANT NAMED 'FIREFLY'**

(50) Latin Name: ***Coreopsis* hybrid**
Varietal Denomination: Firefly

(71) Applicant: Terra Nova Nurseries, Inc., Canby, OR (US)

(72) Inventor: Harini Korlipara, Canby, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 101 days.

(21) Appl. No.: 14/120,301

(22) Filed: May 14, 2014

(65) Prior Publication Data

US 2015/0334907 P1 Nov. 19, 2015

(51) Int. Cl.
*A01H 5/02* (2006.01)

(52) U.S. Cl.
USPC ..... Plt./417

(58) Field of Classification Search
USPC ..... Plt./417
See application file for complete search history.

*Primary Examiner* — June Hwu
(74) *Attorney, Agent, or Firm* — Klarquist Sparkman, LLP

(57) ABSTRACT

A new and distinct *Coreopsis* plant named 'Firefly' characterized by daisy-type inflorescences that grow to 4 cm in diameter, inflorescences that are bright yellow with dark red eyes, hardy to Zone 6 (maybe lower), grass green foliage on short stems, flowering for the whole summer, a very compact, mounding habit, and excellent vigor.

1 Drawing Sheet

Botanical denomination: *Coreopsis* hybrid.
Variety designation: 'Firefly'.

BACKGROUND OF THE INVENTION

The present invention relates to a new and distinct *Coreopsis* and given the cultivar name 'Firefly'. *Coreopsis* is in the family Asteraceae. This new cultivar originated from a controlled breeding program to produce hardy compact *Coreopsis*. The new cultivar originated from planned cross of two proprietary unnamed *Coreopsis verticillata* hybrid seedlings. The new cultivar of *Coreopsis* is an herbaceous perennial to be grown for landscape and container use in a sunny site.

Compared to the parent seedlings the new variety is much shorter with larger flowers and a more upright habit.

Compared to *Coreopsis* 'Bengal Tiger', U.S. Plant Pat. No. 23,345, the new cultivar is much more compact, with smaller flowers that have darker yellow color and a smaller more concentrated red center.

SUMMARY OF THE INVENTION

The following traits have been repeatedly observed and are determined to be the unique characteristics of the new variety. These characteristics in combination distinguish *Coreopsis* 'Firefly' as a new and distinct cultivar:

1. daisy-type inflorescences that grow to 4 cm in diameter,
2. inflorescences that are dark yellow with dark red eyes,
3. hardy to Zone 6, maybe lower,
4. grass green foliage on short stems,
5. flowering for the whole summer,
6. a very compact, mounding habit, and
7. excellent vigor.

This new cultivar has been reproduced only by asexual propagation (cuttings and tissue culture). Each of the progeny exhibits identical characteristics to the original plant. Asexual propagation by cuttings and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

FIG. 1 shows a group of nine-month-old *Coreopsis* 'Firefly' growing in the ground in the trial field in late July in Canby, Oreg.

DETAILED PLANT DESCRIPTION

The following is a detailed description of the new *Coreopsis* cultivar based on observations of nine-month-old specimens growing in the trial beds in full sun in Canby, Oreg. Canby is Zone 8 on the USDA Hardiness map. Temperatures range from a high of 95° F. in August to 32° F. in January. Normal rainfall in Canby is 42.8 inches per year. The color descriptions are all based on *The Royal Horticultural Society Colour Chart*, $5^{th}$ edition.

Plant:

*Type*.—Herbaceous perennial.
*Hardiness*.—USDA Zones 6 to 9.
*Size*.—35 cm wide and 27 cm tall to top of inflorescences.
*Form*.—Mound.
*Vigor*.—Excellent.
*Roots*.—Fibrous, stems root easily from stem cuttings.

Stem:

*Type*.—Ascending, well branched.
*Size*.—Grows to 17 cm tall to where branches for flowering and 5 mm wide.
*Number of stems from the crown*.—30.

*Branching habit*.—Freely branched, an average of 8 lateral branches with secondary branches, branches are opposite in arrangement, new lateral flowering branches are continuously produced throughout the summer.

*Internode length*.—1 cm to 3.5 cm.

*Surface*.—Glabrous.

*Color*.—Green 138B.

Leaf:

*Type*.—Simple.

*Shape*.—Pinnately 3 parted with thread-like segments, to linear on top leaves.

*Arrangement*.—Opposite.

*Size*.—Thread-like segments can spread to 3 cm wide and 4 cm long, the linear segments can grow to 40 mm long and 2 mm wide.

*Apex*.—Acute.

*Margins*.—Entire.

*Petiole*.—0 mm to 2 mm long and 1 mm wide, Green 137B.

*Surface texture*.—Glabrous on top and sparsely pubescent on bottom side.

*Venation*.—Pinnate, visible main vein the same color as the leaf on both sides.

*Color*.—Topside Green 137A, bottom side Green 137B.

Inflorescence:

*Type*.—Long stalked terminal heads of daisy type inflorescences.

*Peduncle*.—Grows to 3.5 cm long, 1 mm wide, glabrous, Green 137A.

*Size*.—Grows to 4 cm wide and 10 mm deep.

*Immature* (*i.e. the "flower bud"*).—Globular, 4 mm wide and 4 mm deep, Yellow Green 152B, glabrous.

*Receptacle*.—Disc shaped, 3 mm wide and 1.2 mm deep, Yellow Green 145B.

*Phyllaries*.—Series not distinct; usually 9 lobes in number, in an area 3 mm deep and spreading 6 wide mm wide, each lobe linear, 2 mm to 4 mm long and 1 mm wide, margin entire, tip acute, glabrous on both sides, both sides Green 137A.

*Lastingness*.—Each inflorescence lasts about a week on the plant.

Florets:

*Type*.—Composite.

*Ray florets*.—8 in number with no pistil or stamen, grows to 21 mm long, 7 mm wide, obovate, with the tip acute and top ⅓ sometimes irregularly notched, side margins entire, glabrous on both sides; topside Yellow 7A on top ⅔, Greyed Purple 187B on bottom third, bottom side Yellow 5A on top ⅔ to Greyed Yellow 161A on bottom third.

*Disc*.—Flat becoming rounded with maturity, 5.5 mm wide and becoming 4 mm deep with maturity, Greyed Purple 187B.

*Disc florets*.—Tubular, with stamen and pistil, about 40 in number, 8 mm long and 1 mm wide, tubular; corolla 5.5 mm long, 5 lobed, tube Yellow 4C, lobes Greyed Purple 187A; pistil 1, 8 mm long, ovary 2 mm long, Green Yellow 1C, style 5 mm long, with extruding, 2-branched stigma, stigma and style Yellow Orange 22A; stamen 5, anthers 1.2 mm long, Greyed Brown N199B, pollen none.

*Bloom period*.—June through frost in Canby, Oreg.

*Fragrance*.—None.

*Seed*.—None seen.

*Fertility*.—Poor.

Disease and pests: No pests or diseases have been observed on plants grown under commercial conditions in Canby, Oreg. No resistances are known.

I claim:

1. A new and distinct *Coreopsis* plant as herein illustrated and described.

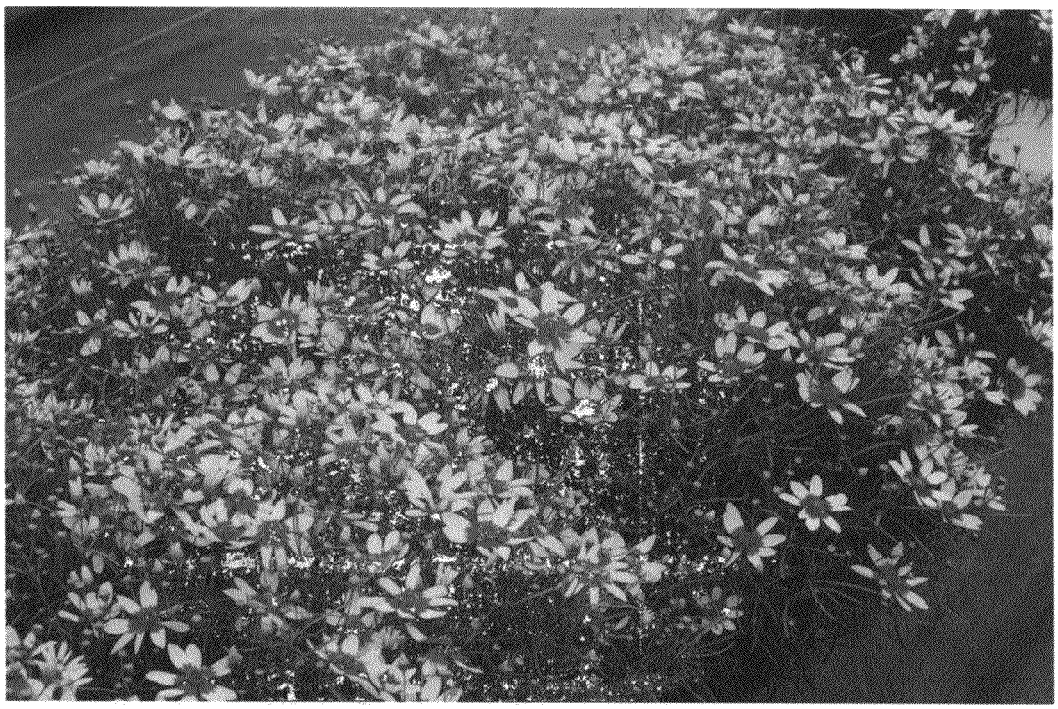

* * * * *